(12) United States Patent
Alexander et al.

(10) Patent No.: US 7,515,269 B1
(45) Date of Patent: Apr. 7, 2009

(54) SURFACE-ENHANCED-SPECTROSCOPIC DETECTION OF OPTICALLY TRAPPED PARTICULATE

(75) Inventors: Troy A. Alexander, Federalsburg, MD (US); Paul M. Pellegrino, Columbia, MD (US); James B. Gillespie, Ellicott City, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 55 days.

(21) Appl. No.: 11/049,583

(22) Filed: Feb. 3, 2005

Related U.S. Application Data (60) Provisional application No. 60/541,398, filed on Feb. 3, 2004.

(51) Int. Cl.
*G01N 21/55* (2006.01)
(52) U.S. Cl. ...................................... 356/445
(58) Field of Classification Search .................. 356/326, 356/301, 302
See application file for complete search history.

(56) References Cited

U.S. PATENT DOCUMENTS

| | | | |
|---|---|---|---|
| 5,864,397 A | 1/1999 | Vo-Dinh | |
| 6,313,914 B1 | 11/2001 | Roe | |
| 6,770,488 B1 | 8/2004 | Carron et al. | |
| 6,795,777 B1* | 9/2004 | Scully et al. | 702/28 |
| 2004/0012778 A1* | 1/2004 | Li et al. | 356/301 |
| 2005/0040455 A1* | 2/2005 | Bozano et al. | 257/314 |

OTHER PUBLICATIONS

Creely et al. "Dual wavelength optical tweezers for confocal Raman spectroscopy" 2005, Optics Communications, pp. 465-470.*
Ashkin et al. "History of Optical Trapping and Manipulation of Small-Neutral Particle, Atoms, and Molecules". IEEE Journal on Selected Topics in Quantum Electronics. vol. 6, No. 6, Nov./Dec. 2000.*
Gebner et al. "Identification of Biotic and Abiotic Particles by Using a Combination of Optical Tweezers and In Situ Raman Spectroscopy", ChemPhysChem 2004, pp. 1159-1170.*
Xie et al. "Near-infrared Raman spectroscopy of single optically trapped biological cells", Optics Letters, vol. 27, No. 4, Feb. 15, 2005.*

(Continued)

*Primary Examiner*—Tarifur Chowdhury
*Assistant Examiner*—Tara S Pajoohi
(74) *Attorney, Agent, or Firm*—William V. Adams; Christos S. Kyriakou (57) ABSTRACT

A method of particle detection includes optically trapping a single particle having an averaged linear dimension of between 0.10 microns and 50 microns in a focal region optical trap formed from a trap visible to near-infrared wavelength. The trap is proximal to a substrate having a discontinuous metal coating so as to exploit a surface plasmon resonance generated electric field caused by irradiation of the metal coating. The single particle is then exposed to an interrogation wavelength to yield scattering spectrum relating to the particle. A particle identification digital database containing scattering spectra from a variety of different single particles that vary in spectral features facilitates identification of unknown spectra. A microfluidic cell is detailed to facilitate the automated scanning of numerous particles from a sample.

12 Claims, 7 Drawing Sheets

OTHER PUBLICATIONS

A. Ashkin, Physical Review Letters, 24, 156 (1970).
A. Ashkin et al., Optics Letters, 11, 288 (1986).
A. Ashkin et al., Science, 235, 1517 (1987).
A. Ashkin et al., Nature, 320, 769 (1987).
A. Ashkin et al., Nature, 348, 346 (1990).
W. H. Wright et al., IEEE J. of Quantum Electronics 26, 2148 (1990).
M. Ericsson et al., J. Bacteriol. 182, 5551 (2000).
C. Xie et al., Optics Letters, 27, 249 (2002).
J. Guck et al., Biophysical Journal, 81, 767 (2001).
A. Resnick, Review of Scientific Instruments, 72, 4059 (2001).
M. Lankers et al., Chemical Physics Letters, 277, 331 (1997).
J. F. Lubben et al., Journal of Molecular Structure, 480-481, 311 (1999).
V. E. Roman et al., Journal of Molecular Structure, 482-483, 497 (1999).
K. Ajito et al., Analytical Chemistry, 72, 4721 (2000).
K. Ajito et al., Applied Spectroscopy, 56, 541 (2002).
M. P. Houlne et al., Analytical Chemistry, 74, 4311 (2002).
J. R. Ferraro et al., Introductory Raman Spectroscopy, (Academic Press, San Diego and London, 1994), Chapter 3.
D. L. Gerrard et al., Organic and Petrochemical Applications of Raman Spectroscopy, (John Wiley and Sons, Inc., New York, 1991), 301-304.
K. Grabar et al., Analytical Chemistry, 67, 735 (1995).
W. H. Woodruff et al., Biochemical and Biophysical Research Communications, 58, 197 (1974).
H. Shibata et al., Microbiology and Immunology, 30, 307 (1986).
R. Manoharan et al., Journal of Microbiological Methods, 11, 1 (1990).
E. Ghiamati et al., Applied Spectroscopy, 46, 357 (1992).
M. O. Scully et al., Proceedings of the National Academy of Sciences of the United States of America, 99, 10994 (2002).
A. E. Grow et al., Journal of Microbiological Methods, 53, 221 (2003).
L. G. Olson et al., Analytical Chemistry, 73, 4268 (2001).
G. W. Gould et al., The Bacterial Endospores, (Academic Press, London and New York, 1969), Chapter 7.
L. Dawei et al., Spectrochimica Acta, 43A, 379 (1987).
X. Wang et al., Spectrochimica Acta, 53A, 2495 (1997).
S. Sekulic et al., Anal. Chem., 65, 835A (1993).
W. Lindberg et al., Anal. Chem., 55, 643 (1983).
D. M. Haaland et al., Anal. Chem., 60, 1193 (1988).
D.M. Haaland, Anal. Chem., 60, 1208 (1988).

* cited by examiner

SURFACE-ENHANCED-SPECTROSCOPIC DETECTION OF OPTICALLY TRAPPED PARTICULATE

RELATED APPLICATIONS

This application is a utility application claiming priority of U.S. provisional application 60/541,398 filed Feb. 3, 2004.

GOVERNMENT INTEREST

The invention described herein may be manufactured, used, and licensed by or for the United States Government.

FIELD OF THE INVENTION

This invention in general relates to a method and system for particulate optically trapped SERS characterization and in particular, to a method and system for non-destructive single particle characterization.

BACKGROUND OF THE INVENTION

Particulate analyte characterization is currently limited to averaging techniques that sample a field of particles under comparatively mild sampling conditions, or single particle interrogation techniques that subject the particle to a harsh sampling condition in order to generate a sufficient signal relative to background noise. Unfortunately, many forms of particulate, including organic polymers and biological cells cannot tolerate the spectroscopic techniques needed to characterize them directly. Instead, one resorts to staining or shadowing techniques that are both labor intensive and destructive of the test subject. The time required to characterize particulate also limits the use of such information in rapidly changing situations as diverse as a manufacturing, treating an infection, and managing a contamination event.

Accurate and sensitive detection of viruses and hazardous microorganisms is a requirement in numerous industrial, military, workplace, healthcare and even home environments. A difficulty that arises in biological detection is the relative paucity of molecules that are exclusively found in targets. Additionally, the inability of a single technique to afford definitive characterization through the strain level of the microbe means that culturing the sample is often required thereby increasing the time-consumed in characterization. Animate particulate, such as that found in a forensic setting, simply is not fully characterized.

Since the seminal work of Ashkin in 1970, based on a dual laser beam system (1) and later work in 1986 employing a single laser beam apparatus (2), the laser tweezer phenomenon has been broadly accepted as a powerful tool to study viruses (3), vegetative bacterial cells (4-8), mammalian cells (9) and colloidal crystallization in microgravity environments (10). More recently, this technique in combination with various Raman detection schemes has been applied to the investigation of inorganic gas bubbles (11), aerosols (12), emulsion particle polymerization (13), liquid-liquid extraction of toluene in water (14), organic nanoparticles (15), yeast cells (8) and solid-phase peptide synthesis (16).

Raman spectroscopy has been an invaluable technique in the study of various chemical systems and has become widely accepted as an analytical characterization methodology (17, 18). The attractiveness of this technique stems from the attributes of narrow spectral band structure, lack of interference from water, and relative insensitivity to the excitation wavelength employed. However, un-enhanced Raman spectral features are considered to be relatively weak thus requiring relatively lengthy collection times. In many applications, high quality spectra may be achieved with shortened acquisition times and improved spectral features by exploiting various amplification techniques. Namely, Resonance Raman Scattering (RRS), Surface Enhanced Resonance Raman Scattering (SERRS) or Surface-Enhanced-Raman-Scattering (SERS) (17-19). RRS and SERRS are typically conducted using ultraviolet excitation to facilitate electronic excitation (i.e. strong absorption) in the analyte of interest. Ultraviolet excitation precludes implementation of RRS and SERRS in a single beam optical trapping configuration since the trapped particle experiences $MW/cm^2$ UV intensity levels that coupled with significant UV-light absorption photo-decompose most analytes.

SERS represents another method for enhancing a conventional Raman signal that is operative with less destructive near-infrared optical beam trapping. Currently, the mechanism of the SERS effect is not fully understood; however, a plausible explanation for at least a significant portion of the spectral amplification has been attributed to an increase in the electromagnetic field strength encountered by the analyte. Briefly, this intensified electromagnetic field is generated when a roughened metal surface (typically, Au, Ag, Pt, Pd or Cu) is irradiated with the requisite wavelength of light and metal conduction band electrons are excited to collective oscillation and produce a surface plasmon resonance. The Raman and infrared (IR) signals associated with analytes proximal to such a metal surface have been shown to be enhanced from 4 to 14 orders magnitude relative to un-enhanced Raman (17). Additionally, the enhancement is reversible when the particulate analyte is removed from the metal surface. In spite of these features, SERS has gained only limited acceptance since early reports on this technique in the late 1970's. This limited acceptance is in large part due to the lack of fabrication reproducibility in most SERS substrates. Relatively recent advances in SERS-active substrate fabrication have addressed this reproducibility issue. Specifically, these substrates are easily wavelength adjustable, durable, biocompatible and possess a long shelf-life (19).

Bacterial spore characterization is a subset of particulate characterization where the limitations of current techniques are profound. Endospores are an alternate cell form of various bacterial genera including *Bacillus, Clostridium, Desulfotomaculum, Oscillospira, Sporosarcina, Sporolactobacillus*, and *Thermoactinomyces*. An endospore is formed as an adaptive response to environmental conditions unfavorable to the bacterial cell form, such as dehydration, limited nutrient availability and extreme temperatures. While endospores are themselves metabolically inactive, they are activated under appropriate conditions, forming an active vegetative bacterial cell. Thus, the presence of an endospore is indicative of a potential biohazard and therefore endospore detection is a desirable goal.

Over the past three decades Raman spectroscopy has been employed to study various *Bacillus* spore species. Due to the relatively meager Raman scattering cross-sections exhibited by many biological materials, a majority of this reported work has been conducted using various Raman amplification techniques. Specifically, early work in this area was based on the Resonance-Raman-Scattering (RRS) technique utilizing ultraviolet (i.e., 222 nanometer) to green (i.e., 514.5 nanometer) laser excitation sources (20-23). More recently, reports have been published describing the implementation of Femtosecond Adaptive Spectroscopic Techniques applied to Coherent-Anti-stokes-Raman-Spectroscopy (FAST CARS) (24) as well as SERS microscopy (25). These various Raman spectroscopies have been applied to the study of bulk endospore samples and have failed to afford information sufficient to distinguish between strains of the same endospore.

Thus, there exists a need for a non-destructive characterization technique for single particles. The ability to characterize a single particle in a non-destructive manner confers the ability to examine particulate changes over time and to assess population diversity.

SUMMARY OF THE INVENTION

A method of particle detection includes optically trapping a single particle having an averaged linear dimension of between 0.10 microns and 50 microns in a focal region optical trap formed from a trap visible to near-infrared wavelength. The trap is proximal to a substrate having a discontinuous metal coating so as to exploit a surface plasmon resonance generated electric field caused by irradiation of the metal coating. The single particle is then exposed to an interrogation wavelength to yield scattering spectrum relating to the particle.

A particle identification system is provided that includes a digital database containing scattering spectra from a variety of different single particles that vary in spectral features. An algorithm applies a chemometrics protocol to an unknown particle spectrum to determine the relationship between the unknown particle spectrum and one or more standards spectra from the database. A computer is provided to run the algorithm and access the database. A user interface is coupled to the computer for manual data entry. A particle identification system is particularly well suited for endospore particles since the genealogy of a virulent endospore is critical in rapidly identifying the source of the outbreak.

A microfluidic cell is detailed to facilitate the automated scanning of numerous particles from a sample. The cell includes a vessel having a spectroscopic sampling region defined by a wall. The spectroscopic sampling region has a sampling cross sectional dimension and is transmissive to at least one of ultraviolet, visible, and near infrared radiation. The sampling region is in fluid communication with a sample buffer region that has a larger cross sectional dimension than the sampling cross sectional dimension. A discontinuous metal coating is applied to the backwall of the spectroscopic sampling region. A fluid injector drives a fluid from the buffer region to the sampling region until a particle is detected within the sampling region. This process is repeated to scan numerous single particles in an automated fashion. A statistically meaningful characterization of the total sample is achieved in this manner.

DESCRIPTION OF THE PREFERRED EMBODIMENTS

The present invention has utility in the detection of single particles or a solvent volume under conditions that are unlikely to impair biological particle viability or modify inanimate particle chemical properties. The present invention in providing a spectroscopic fingerprint of a single particle has utility in settings illustratively including food processing and medical diagnosis where the presence of particular bacteria, endospores, or viruses are indicative of contamination or infection; manufacturing process control of particulate materials; biohazard monitoring and response; reaction monitoring of particle reaction in the presence of possible reactants; intra-particle morphological change mechanisms; and forensic investigations as to the origin of a particle.

Collection of a scattering spectrum from a single particle is enhanced by spectrum collection in proximity to a discontinuous metal coating that generates a surface plasmon resonance signal upon irradiation. Through adjustment of the distance between the particle and the discontinuous metal coating, the spectrum collected is representative of different portions of the particle thereby allowing the collection of surface weighted spectra, as compared to a particle volume averaged spectrum. Distance adjustment between the discontinuous metal coating and the optical trap is most easily performed through supporting the substrate on a microscope stage and moving the stage relative to the optical trap. Alternatively, the optical trap is translated with an optical tweezers.

As used herein "particle" or "particulate" are synonyms defined to include a domain distinct from a surrounding solvent and having an averaged linear dimension over the three orthogonal axes of between 0.10 and 50 microns for a single domain or an aggregate domain. A particle suitable for spectral interrogation according to the present invention illustratively includes a eukaryotic cell, a bacterium, a virus, a polymer strand, an organelle, a colloid, and a nanocrystal. While an individual particle is routinely suspended alone in an optical trap for spectral investigation, it is appreciated that a particle can be adhered to the surface of another type of particle to adjust the average linear dimension. By way of example, a virus particle or multiple virus particles can be adhered to a colloidal particle surface or a target cell and the resulting aggregate particle is amenable to spectral interrogation according to the present invention. Colloidal silica is particularly well suited for aggregate particle formation. Likewise, ribosomes, antibodies, or nanocrystals having an average linear dimension of less than 0.10 microns are adhered to a colloidal particle surface by conventional techniques. These techniques include the use of an intermediate coupling agent such as biotin, thiols, epoxides, and organosilanes.

According to the present invention, an optical trap is formed in the focal region of a microscope objective with visible or near-infrared laser light to maintain a particle within the trap volume. Through the use of a translation stage, an optical trap functions as optical tweezers, allowing the movement of a trap relative to the point of trap formation. Optical tweezer physics and properties are well known (2). The near-infrared optical tweezers are combined with an incident interrogation wavelength that is used to generate a scattering spectrum from the particle in proximity to a discontinuous metal surface.

Figure 1:
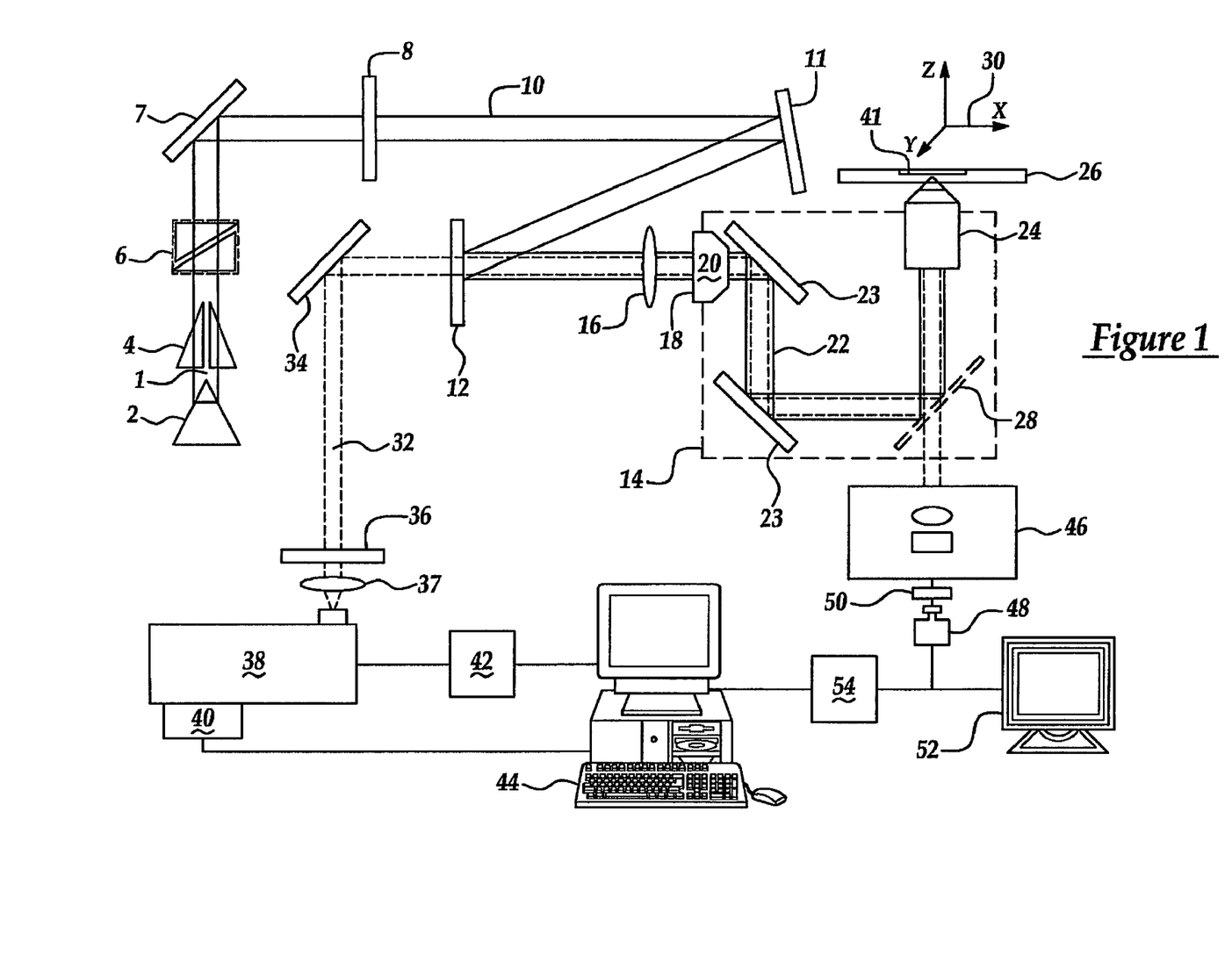
FIG. 1 is a schematic illustrating components of an inventive Near-Infrared Raman-Tweezer Detection System (NIR-RTDS)

A preferred component schematic for performing an inventive method of particle detection is shown in FIG. 1, as Near-Infrared Raman Tweezer Detection System (NIR-RTDS). Related beam path and component configurations are known to the art (9,11,12,14-16). A 787 nanometer light 1 from a commercially available temperature controlled, laser diode 2 (Thor Labs) capable of 50-mW output power is collimated through a Faraday optical isolator 4 (Electro-Optics Technology, Inc; Model #LD381780) and a circularizing anamorphic prism pair 6 (Thor Labs) before passing being reflected from a mirror 7 and through an interference filter 8 (Omega Optical; p/n 785DF10) with better than 70% transmission at 785 nanometers. The resulting circular beam 10 is then reflected by a mirror 11 and a holographic filter 12 (SuperNotch-Plus™, Kaiser Optical Systems, Inc.; p/n HSPF-785.0AR-1.0) centered at 785.0 nanometers into an inverted microscope 14 (TMS, Nikon). A 50 millimeter focal length lens 16 (Thor Labs, p/n LA1131-B) is placed before the microscope 14 to expand the laser beam 10 and efficiently fill the back aperture 18 of the focusing objective 20. This expanded beam 22 is then reflected by mirrors 23 to be focused by a 100× oil immersion microscope objective 24 (Nikon TE 300, N. A. 1.25) into the sample containing the target particle 26 with a spot size of 1-2 microns at the focus (with an intensity of ~0.5 $MW/cm^2$ at the beam focus). A dichroic mirror 28 is placed inside of the microscope 14, before the sample 26 to deflect the beam 22 into the microscope objective 24. The position of the sample 26 is controlled in three dimensions using piezoelectric-driven actuators represented at 30 (Model 8302; New Focus, Inc.) having a minimum linear motion of less than 30 nanometers.

Both Rayleigh and inelastic scattered light (dashed line) 32 from the single, trapped particle 26 is collected by the same 100× oil immersion objective 24 and collimated onto and directed by the dichroic mirror 28 through the holographic filter 12, an intermediate mirror 34, a second holographic filter 36 before being focused by a lens 37 onto the entrance slit of a 0.275 meter polychromator 38 (SpectraPro®-275, Acton Research Corporation) and liquid nitrogen-cooled, back illuminated charge coupled device (CCD) 40 (Spec-10: 100BR, Roper Scientific) for spectral analysis. The holographic filters have optical densities better than 6.0 so as to remove the majority of Rayleigh scattering. The scattered light 32 is enhanced by placing the sample 26 in proximity with a discontinuous metal coating 41. Light 32 coupled into the polychromator 38 is laterally dispersed across the 1340× 100 pixel CCD 40 by a 1200 groove/mm grating (not shown) within the polychromator 38, the grating is blazed at 750 nanometers. The polychromator 38 is controlled through a digital-to-analog converter 42 and data is collected from the CDD 40 by a personal computer 44 though a 16-bit interface card (not shown) using the WinSpec/32™ software package (Version 2.5.8.1, Roper Scientific). To increase the signal to noise (S/N) ratio the output of the CCD 40 is vertically binned prior to readout. The area immediately surrounding the optical trap in the sample 26 is imaged through the microscope objective 24 and imaging optics 46 (Edmund Industrial Optics) by a near infra-red-sensitive video camera 48 (NEC TI-24A). A reflective neutral density filter 50 is placed before the camera 48 to further reduce the amount of laser light reaching the camera. Images from this video camera 48 are displayed on a video monitor 52 for observation and digitized for later inspection using an 8-bit analog-to-digital framegrabber 54 (PixelSmart, Lewiston N.Y.).

The schematic of FIG. 1 operates to provide surface enhanced Raman scattering from a particle within the optical trap volume. The use of a single near infra-red laser light source and optical path, as shown in FIG. 1, to provide the optical trap and simultaneously interrogate the particle to create scattered light is preferred as a comparatively simple and inexpensive optical system for performing the methods according to the present invention. It is appreciated that additional information is available from an optically trapped particle when the interrogation beam is of a different: wavelength, incident angle to the particle, pulse time-scale, or a combination thereof relative to the near infra-red optical trapping wavelength. By way of example, a femtosecond interrogation pulse incident on the particle having a different wavelength than the near infra-red optically trapping wavelength affords information about the particle on a time scale where the resulting spectra is largely independent of particle rotation and movement within the trap. It is appreciated that the trapping beam and interrogation beam while utilizing the same optical train need not be of the same wavelength, and an angle can be created between the trapping beam and interrogation beam through the use of an acousto-optic deflector or a servo-mirror. The angle can range from 0 (collinear) to twenty degrees, with the microscope objective numerical aperture being a determining factor.

For surface-enhanced Raman scattering, the interrogation light source is selected to generate radiation having a wavelength that causes appreciable Raman-scattering in the presence of the particle being measured. Although it is known that Raman-scattering occurs essentially at all wavelengths, preferably, the radiation employed is near-infrared radiation since ultra-violet radiation is associated with parasitic fluorescence. Typically interrogation wavelengths range from 320 to 1700 nanometers. Preferred interrogation wavelengths range from 650 to 1100 nanometers. Laser diodes are commercially available to select numerous specific laser lines within the preferred interrogation wavelength range. It is appreciated that longer wavelengths such as 1064 nanometers are operative herein provided that a InGaAs detector is employed. This detector is operative to 1700 nanometers.

A discontinuous metal coating has a high surface area to volume ratio and is fabricated on a surface of the substrate by conventional means including, for example, magnetron sputtering, plasma sputtering, and electron-beam evaporation. The metal is selected to create a large diameter surface plasmon resonance electric field under illumination by either the trap wavelength or the interrogation wavelength. Discontinuous metal coatings are illustratively formed from gold, silver, platinum, palladium, copper, and alloys thereof. The coating typically has an average thickness of about 0.02 micron to 2 microns and preferably about 0.02 microns to 0.5 micron. Electrically conductive colloidal material is readily synthesized from gold, silver, platinum, palladium, copper, and alloys thereof by reduction of aqueous metal salts in the presence of a passivating ligand or a coordinating solvent or etching of a uniform film to for a nanoporous coating. Alternatively, carbon or silica grains coated with the electrically conductive material. The electrically conductive colloidal material typically has an averaged linear dimension over the three orthogonal axes ranging from 10 to 10,000 nanometers and preferably from 30 to 100 nanometers.

Figure 2A:
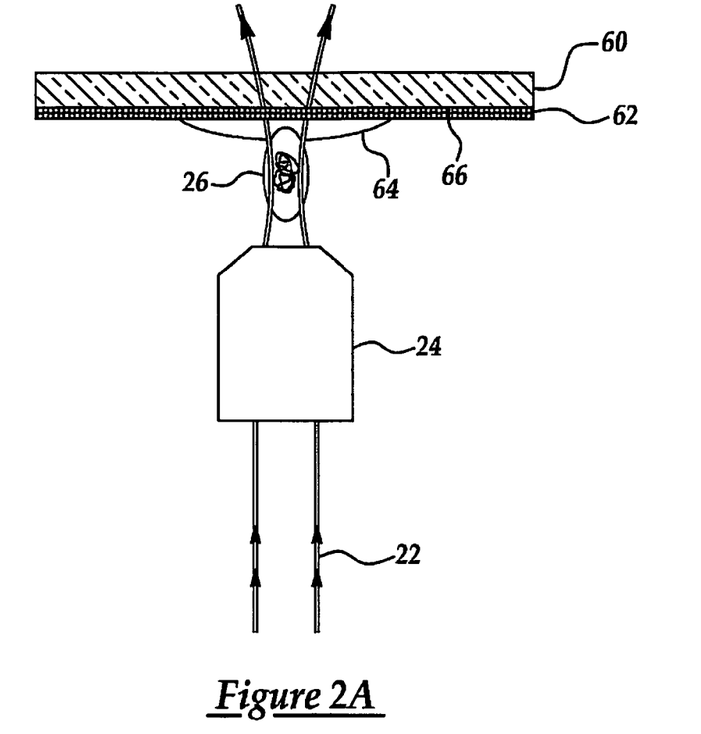
FIG. 2A. is a cross-sectional schematic view of the optically trapped particle and the proximal substrate having a discontinuous metal layer thereon according to FIG. 1.

FIG. 2 shows cross-sectional schematic view of the optically trapped particle and the proximal substrate having a discontinuous metal layer used to measure a SERS spectrum of a single particle according to FIG. 1; where like numerals correspond to those previous described with respect to FIG. 1. A three-dimensionally trapped liquid sample volume containing the target particle 26 is captured and vertically translated towards a microscope slide 60 that has gold colloid-coating 62. The expanded near infra-red beam 22 transmitted through and around the spore subsequently excites the downward-directed Surface Plasmon Resonance (SPR) generated electric field 64 of the proximal immobilized colloidal mass 62. The SPR-generated electric field 64 extends only a short distance of a few hundred of nanometers away from the substrate surface 66 and only partially overlaps the sample containing the target particle 26. It is appreciated that dimensions of the SPR field is a function of the identity of the metal, the intensity of the beam 22, and the wavelength of the beam, and the domain size of the colloids making up the discontinuous metal coating 62. As such, the dimensional extent of the SPR electric field 64 can be modulated to change the portion of the trap that has the scattering signal therefrom enhanced. This property is exploited to collect a scattering signal that is enhanced for only a portion of the particle. In the case of endospores studies, this allows one to only enhance the scattering signal associated with the endospore coat and not the entire endospores. Thus, one selectively probes the endospore coat. This is attractive attribute regardless of the nature of the particle since it facilitates the isolation and study of particle surface constituents through non-physical means. This attribute coupled with the ability to collect a spectrum from a single particle facilitates studying the same individual particle in different spectroscopic and physical environments. Thus conventional Raman and SERS are readily collected from the same particle, in pure water and in the presence of an additive. This allows the investigation of particles while eliminating particle-to-particle composition variability.

Additives that are operative herein illustratively include a second particle that is the same or different than the single particle, a reactant towards the single particle, a metabolite of the single particle, and a toxin towards said single particle. The case of a bacterium or an endospore the presence of another cell or virus is effective in observing if there is inter-cellular communications to trigger a change in the single particle. Additionally, besides the inter-cellular exchange of messenger molecules, cells are known to emit compounds cytotoxic to all, but closely related cells. Such observations are helpful developing treatments and lysis mechanisms against pathogenic cells. The value of studying the effect a given molecular reactant has on a particle is not confined to biological cells, conformational or electrical changes associated with polymer strands; inorganic platelets, such as bentonite clays, and magnesium hydroxide; semiconductor nanocrystals, and other systems represents a valuable research and quality control function. By way of example, the introduction of a silver metal ion serving as a surface trap quencher would be observed in the SERS spectrum of a 100 nanometer CdSe nanocrystal.

In some situations, it is desirable to detect particles such as bacterial endospores in environments other than those found or maintained at room temperature. For example, it may be of interest to detect bacterial endospores in cold storage compartments, or in heated facilities or reaction chambers. In such cases a suitable solvent is selected that has a melting temperature such that the solvent is in the liquid state at the ambient temperature in the environment to be tested. Suitable solvents for extreme temperature range spectroscopy according to the present invention are well known to the art and illustratively include glycols; glymes; ionic liquids; liquefied gases such as nitrogen; and alcohols. Through appropriate choice of solvent, particles can be detected according to the present invention in the range between −200 to 200 degrees centigrade.

An environmental sample is needed to produce a sample containing a single particle. An environmental sample is in any of various forms such as a gas, an aerosol, a liquid, a solid and a suspension. Methods of obtaining environmental samples are known and include such techniques as dry swabbing, wet swabbing, filter collection, impinging of an air or aerosol from the environment to be tested onto a surface for particle capture, such as a solid, liquid or gel capture surface. An example of such a particle capture surface is a gelatin-coated laboratory slide. An environmental sample is optionally acquired over a specified period of time, for example to facilitate identification of a contaminating incident. In a further option, the environmental sample is representative of a specified location of the environment to be tested, so as to facilitate decontamination of the location. In addition, the environmental sample optionally represents a specified portion of the environment, so as to facilitate calculation of the total particle quantity.

In order to transfer a particle from an environmental sample to an optical trap for sampling, the sampling solvent and environmental sample are brought into contact. For example, where an environmental sample is a dry swab of the environment to be tested, the swab may be brought into contact with the sampling solvent, such as by immersion for a suitable time. A suitable time may be determined by using standards with known concentrations of a particle, so as to calibrate the operation of the method under specific conditions.

Figure 2B:
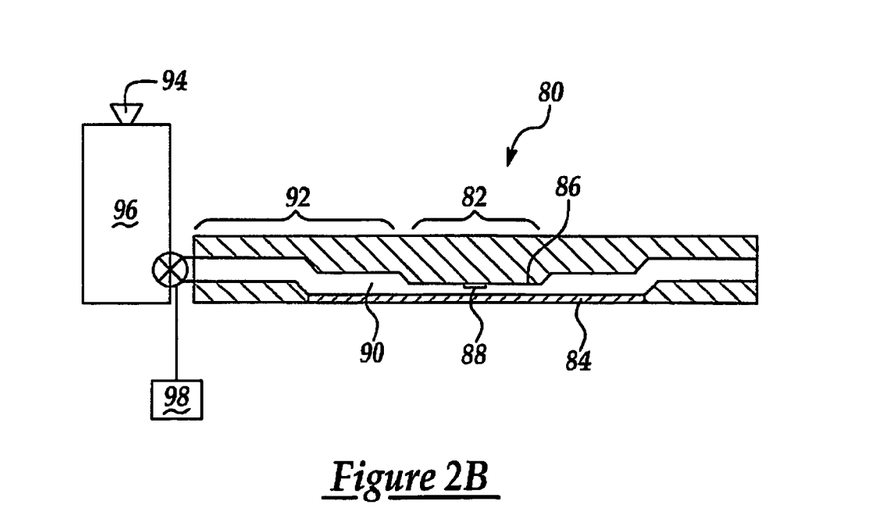
FIG. 2B is a longitudinal cross-sectional schematic view of an inventive microfluidic delivery system for the successive delivery of individual particles from an sample to the SPR-generated electrical field region shown in FIG. 2A.

The accurate transfer of any or all of the particulate within an environmental sample to optical traps for spectroscopic scattering experiments is facilitated through the use of a microfluidic cell as shown generally at 80 in FIG. 2B. The cell 80 has a spectroscopic sampling region 82 defined by a glass front surface 84 and a rear wall glass surface 86 with front and rear directions defined relative to the direction from which the optically trapping near-infrared wavelength is applied. A discontinuous metal coating 88 is applied to the rear wall surface 86. The glass is chosen to have high transmissivity to ultraviolet, visible, and near-infrared light of the wavelengths to be used. It is appreciated that the experimental wavelengths will dictate the choice of surface materials. Quartz glass is particularly well suited for this purpose. The lateral displacement between the front and rear surfaces 84 and 86 typically is between 50 and 250 microns. Preferably, the front and rear surfaces 84 and 86 are both planar and parallel. The linear dimensions of the discontinuous metal coating 88 are between 15 and 240 microns. The metal coating 88 is applied in a variety of shapes including square, rectilinear, and circular. The sidewalls 90 define the cross-sectional dimension of the sampling portion 82. The sampling portion 82 is in fluid communication with a sample buffer region 92, the sample buffer region 92 having a larger cross sectional dimension than the sampling cross-sectional dimension. Preferably, the sample buffer region 92 is stepped backwards relative to the sampling region 82 to inhibit capillary draw along the length of the cell 80. A filter 94 is optionally provided upstream from the sample buffer region 92 to preclude particles beyond a preselected threshold size from entering the buffer region 92.

In use, an environmental sample is solvated with a measured quantity of the trap solvent and the solvent loaded into a sample reservoir 96. The sample reservoir volume is metered through the filter 94 into the buffer region 92 into the sampling region 82 by a fluid injector 98. Upon priming the buffer region 92 single particles can be seized within an optical trap and successively scanned. While the fluid injector can be as simple as a manual micropipette, a capillary electro-osmotic pump is preferred. A capillary electro-osmotic pump draws particles having a charge in an appropriate buffer through a capillary fiber having an electrical bias. In this way continuous particle supply is drawn to the sampling region 82 so that the optical train can be maintained in a continual operational mode. A suitable capillary electrophoresis system is available from Agilent Technology that is adaptable for use as a capillary electro-osmotic pump. The system is amenable to automation so that a statistically significant number of single particles can be spectroscopically scanned. Automation is facilitated by image analysis software that identifies a particle within the optical trap volume imaged by a video camera in FIG. 1 and then translates the optical trap or the cell so that the trap and metal coating are in proximity. Particles that have already been scanned are transported to the opposite end of the sampling region where the volume is collected as a droplet or removed with a micropipette.

A collection of spectra from a variety of particles is readily assembled into a standards database. In addition to the spectra from a given particle, preferably the database also stores characterization information about the particle such as collection specifics, cross-references to characterization derived from other techniques, and images collected through the microscope optics during the scattering experiment. The different spectra in the database are compared to an unknown spectrum for characterization and to identify overlap between the unknown and standards within the database. The digital storage of spectra facilitates computational normalization and comparison routines. With an inexact match between an unknown spectrum and at least one record found in the standards database, the extent of relatedness is preferably determined with an chemometric algorithm such as a neural network, or Principle Component Analysis (PCA) (30-34). This is especially effective in the instance of particles of biological origin, where evolutionary changes such as mutations are noted as populations diverge. A computer is provided to run the algorithm and access the database. A user interface to the computer and database allows for manual data entry and the manipulation of data as part of a standards fitting routine. Optionally, the database is centralized and remote from the computer and access in via an intranet or the Internet. Preferably, a user has the option to add a new unknown spectrum to the centralized database, such that a subsequent user of the database may be able the provide information about the unknown spectra. A standard fit to the unknown by a subsequent user can trigger notification to the unknown submitter. A standards database is particularly well suited for endospore particles since the genealogy of a toxic endospore is critical in rapidly identifying the source of the outbreak.

The present invention is further detailed with respect to the following non-limiting examples. These examples are intended only to illustrate particular aspects of the invention and in no way limit the scope of the appended claims.

EXAMPLE 1

SERS-active substrates are prepared by a method similar to that suggested by Grabar, Freeman, Hommer and Natan (19) using freshly synthesized 60 nanometer gold colloids. Briefly, standard glass microscope slides are cleaned for 1-h in a bath consisting of 1:4 (v/v) 30% $H_2O_2$ to sulfuric acid bath at 60° C. Subsequent to cleaning, the microscope slides are profusely washed in methanol and stored in fresh $CH_3OH$ until needed. A self-assembled-monolayer (SAM) of 3-Aminopropyltriethoxy silane (APTES; Aldrich Chemical Company) is formed on the cleaned glass substrates by submerging the glass slides in a solution of the silane diluted 1:4 (v/v) in methanol. After 24-h, the APTES-derivatized glass is removed from the silane solution and washed repeatedly (~15x) with methanol to remove any unbound silane from the surface. The APTES-derivatized glass is stored in fresh methanol until needed.

EXAMPLE 2

Gold colloids of 60 nanometer size freshly prepared by a previously published (26) method are coupled to the silanized substrate by immersing the washed glass in the aqueous colloidal suspension for 24-h at room temperature. Subsequent to the colloidal coupling the SERS substrates are washed with and stored in de-ionized water until needed for analysis. UV-visible absorbance measurements (not shown) of these substrates reveal a Surface Plasmon Resonance (SPR) optimally excited with 715 to 775 nanometer light. SERS-substrates fabricated through this method are near optimally excited using the NIR-RTDS.

EXAMPLE 3

*Bacillus stearothermophilus* (ATCC 10149 and ATCC 7953) are purchased from Raven Biological Laboratories, Inc. (Omaha, Nebr.) as 40% ethanol-deionized water suspensions. According to the manufacturer, these spores were prepared by incubation in soybean-casein digest broth at 55 to 60° C. for 7 days. Samples for measurement are prepared by diluting 100 microliters of the spore suspension in 40 milliliters of 18 MΩ deionized water to give a final concentration of $7.5 \times 10^4$ CFU/ml (CFU=colony forming units).

EXAMPLE 4

A series of spectra are collected with a laser excitation power of 20-mW (before the microscope), 500-ms integration, 100 co-additions at a spectral resolution of 7.5 $cm^{-1}$ unless otherwise stated using the system described with respect to FIG. 1.

Figure 3A:
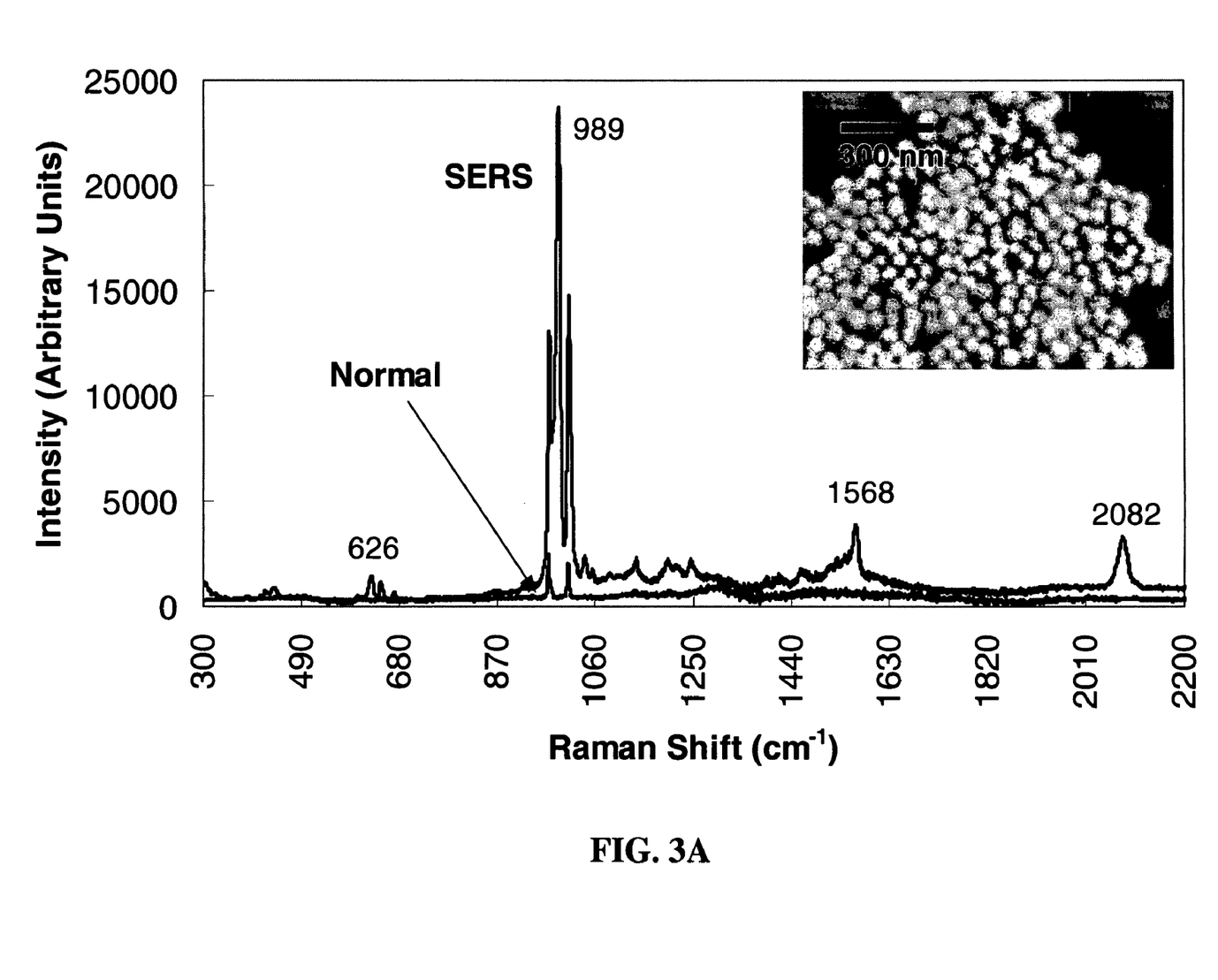
FIG. 3A is a graph of conventional (normal) Raman and Surface-Enhanced-Raman-Scattering (SERS) spectra taken of pyridine using the NIR-RTDS of FIG. 1, the inset is an SEM micrograph of a spectral substrate having 60 nanometer gold colloids immobilized on glass.

The performance of the near-infrared Raman-Tweezer Detection System (NIR-RTDS) of FIG. 1 is estimated by collecting the Raman spectrum (not shown) of a single, optically trapped 2.0 micron diameter polystyrene microsphere suspended in de-ionized water. The background-corrected spectra are in good agreement with published data. Further, the SERS-activity of a representative immobilized gold colloid substrate is ascertained by measuring the spectrum of neat pyridine (relative to de-ionized water) at an immobilized colloidal mass (~50×50 microns) and subsequently measuring the same neat pyridine solution in a vacant (optically transparent) region of the substrate (a few micrometers away from the colloidal mass). As illustrated in FIG. 3A, the SERS spectrum shows the appearance of new bands at 626, 989, 1568 and 2082 cm$^{-1}$ which are not present in the un-enhanced pyridine Raman spectrum. The central band in the ring breathing region at 989 cm$^{-1}$ is especially interesting since it has been reported to be indicative of Surface-Enhancement of pyridine (28,29). That is, the central band in this triplet is present in the pyridine SERS spectrum but not the pyridine normal Raman spectrum. Therefore, the appearance of the 989 cm$^{-1}$ is a good indicator of SERS activity for the substrate. Moreover, the appearance of the band in the pyridine SERS spectrum verifies that the fabricated substrates are in fact SERS-active. Further, these data illustrate a 50-fold signal enhancement in the pyridine SERS spectrum over the pyridine conventional Raman spectrum using the prepared substrates. Depicted in the inset of this FIG. 3A is an SEM micrograph of a gold colloid mass immobilized on glass. The individual gold colloid particles composing the mass are apparent in the image.

EXAMPLE 5

Figure 3B:
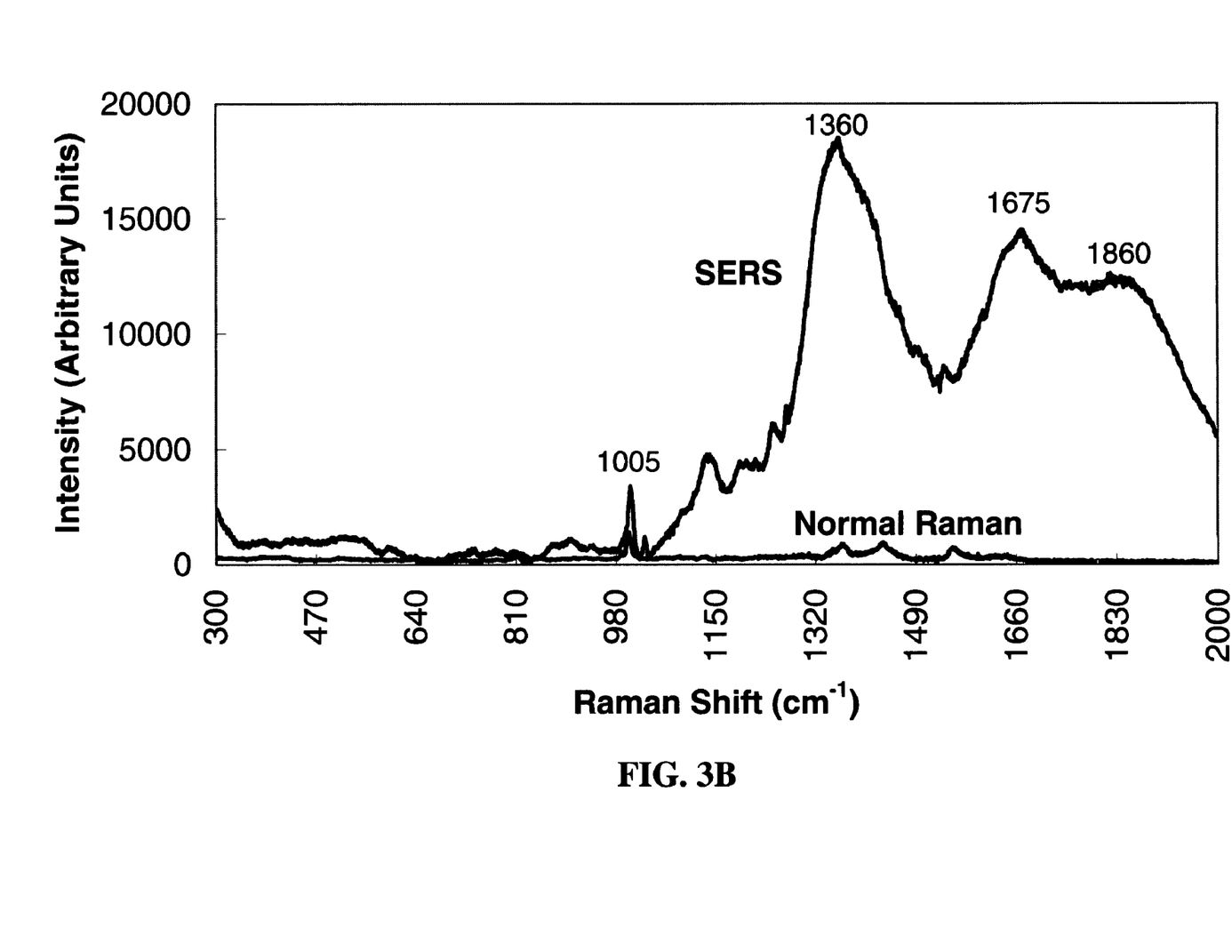
FIG. 3B is a graph of conventional (normal) Raman and Surface-Enhanced-Raman-Scattering (SERS) taken of a single, optically trapped *Bacillus stearothermophilus* (ATCC 10149) spore.

Shown in FIG. 3B are the conventional Raman and SERS spectra for the same optically trapped *Bacillus stearothermophilus* (ATCC 10149) endospore. These spectra are dominated by bands at 1005, 1345, 1434 and 1553 and 1005, 1135, 1246, 1360, 1675 and 1860 cm$^{-1}$ in the conventional Raman and SERS spectra, respectively. Further, the SERS spectrum is enhanced by approximately two orders of magnitude over the conventional Raman spectrum. Additional signal enhancement is observed by positioning the trap in closer proximity to the discontinuous metal coating to facilitate charge transfer between the trapped particle and metal coating. The complexity of these samples (i.e. bacterial endospores) makes it difficult if not impossible to make band assignments. The only assignable band being the dipicolinic acid (DPA) band in the "ring-breathing" region. Specifically, the common band in these spectra at 1005 cm$^{-1}$ is most likely due to dipicolinic acid (DPA), a major constituent of bacterial endospores. A comparison of the SERS and conventional Raman spectra illustrate that the far-Stokes shifted bands in the SERS spectrum are enhanced more than the DPA ring breathing band at 1005 cm$^{-1}$. This can be understood in light that the moieties responsible for these spectral features most probably experience a stronger electric field than DPA. Since the DPA band and the far-Stokes shifted bands in the conventional (i.e., whole spore) Raman spectrum are comparable in intensity (i.e., Raman cross-section); the far-Stokes shifted constituents are held closer to the spore surface than DPA.

EXAMPLE 6

Figure 4A:
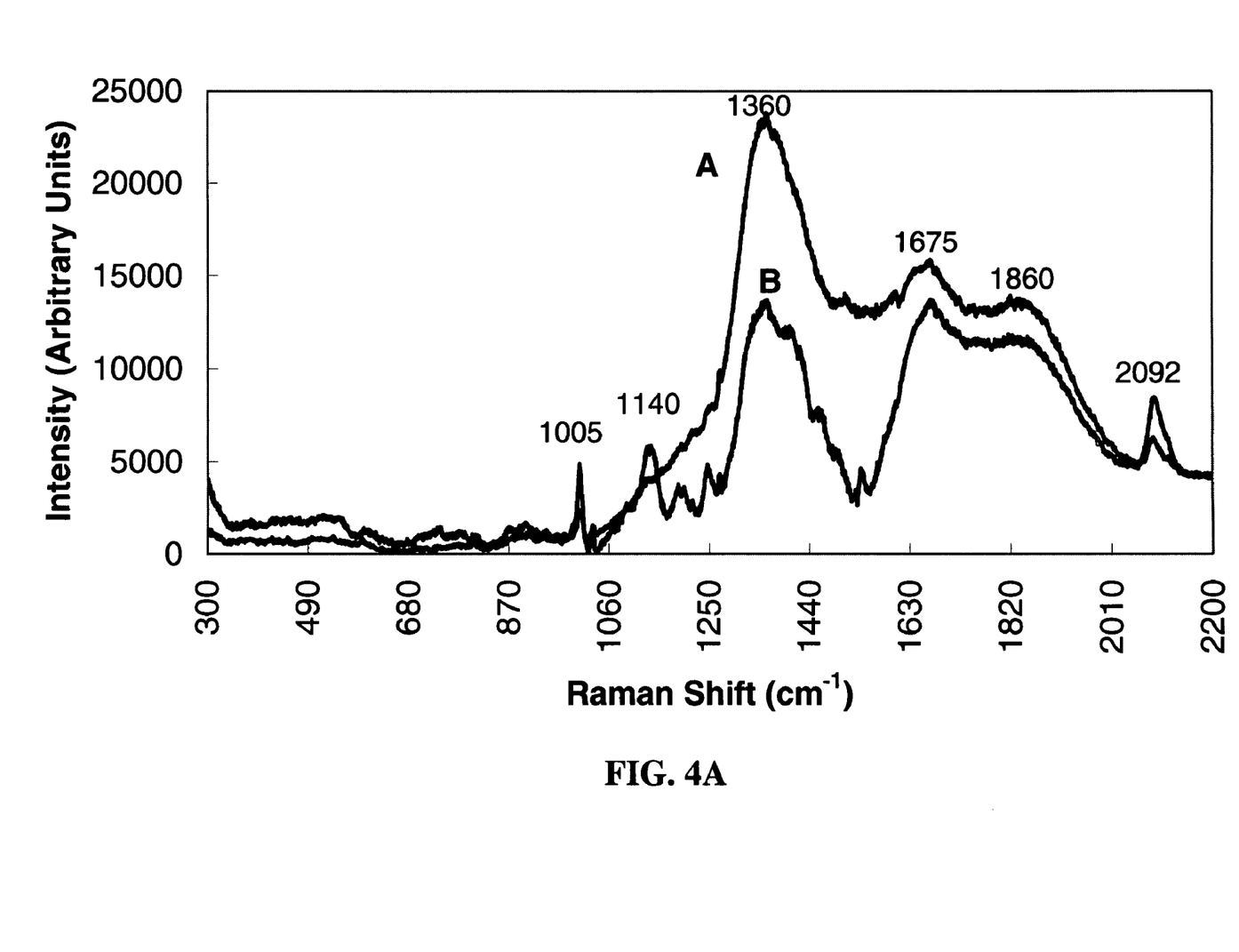
FIG. 4A is a graph of conventional (normal) Raman and Surface-Enhanced-Raman-Scattering (SERS) taken of two different individual, optically trapped *Bacillus stearothermophilus* (ATCC 10149) endospores.

Shown in FIG. 4A are representative SERS spectra for two different optically trapped *Bacillus stearothermophilus* (ATCC 10149) endospores. Only two spectra are shown for clarity. Both spectra are dominated by bands at 1005, 1360, 1675 and 2092 cm$^{-1}$ as well as a pronounced shoulder at 1860 cm$^{-1}$. In general, the shape of these spectra are similar; however, distinct bands at 1140, 1195, 1245 and 1537 cm$^{-1}$ are present in the spectrum labeled B but absent in the A spectrum. Additionally, the band intensity in the B spectrum at 1360 cm$^{-1}$ is much smaller than this band's intensity in the A spectrum. These intensity differences as well as the appearance of pronounced bands in spectrum B in the spectral region from 1060 to 1250 cm$^{-1}$ infer that the distribution and/or relative concentration of Raman-active analytes are different in spore A and spore B. That is, the analytes responsible for the bands between 1060 and 1250 cm$^{-1}$ in spectrum B are held closer to the spore surface and penetrate deeper within the SPR-generated electric field in spore B than in spore A. Further, the pronounced appearance of these bands in spectrum B illustrates the biodiversity present in this spore population.

EXAMPLE 7

Figure 4B:
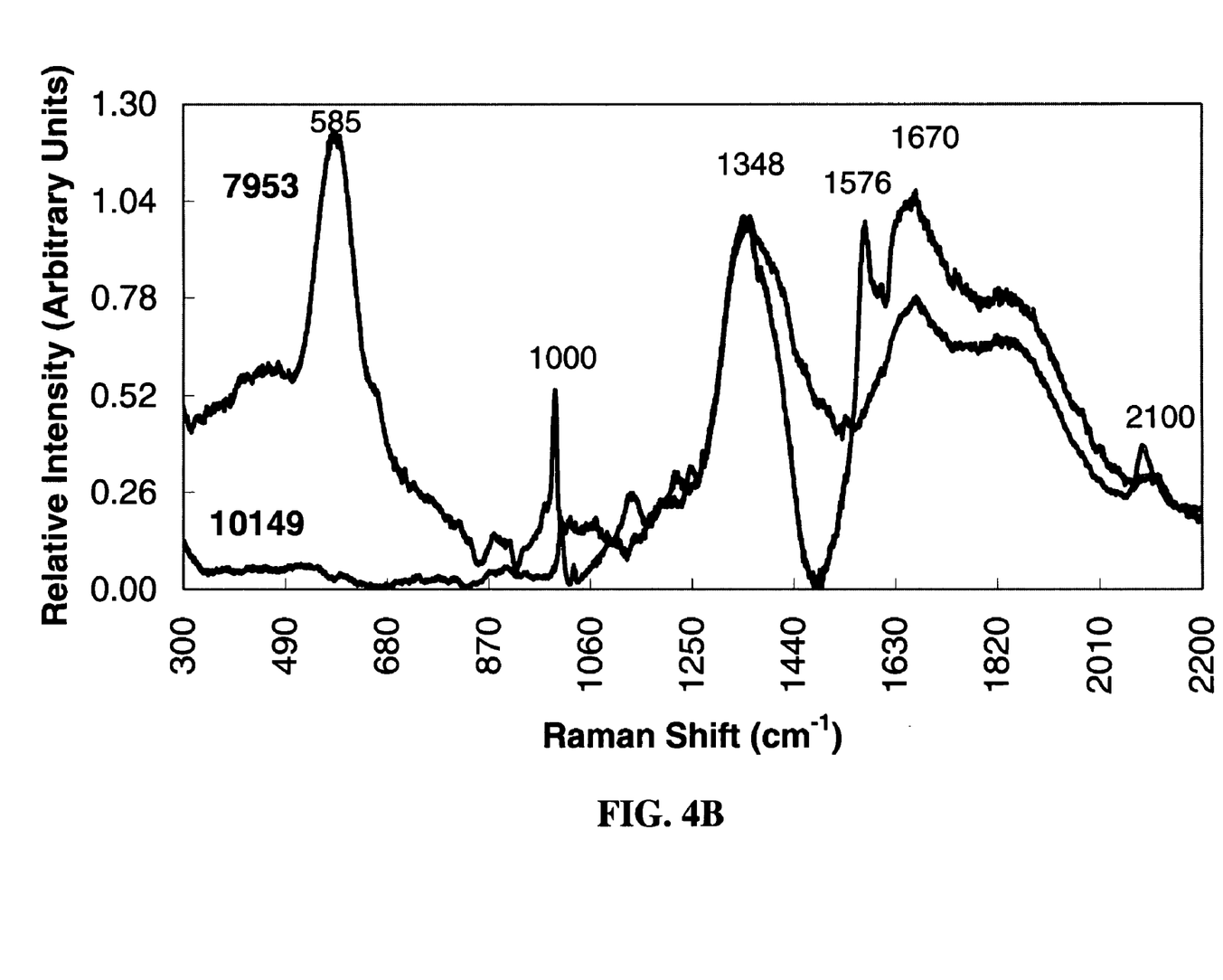
FIG. 4B is a graph of conventional (normal) Raman and Surface-Enhanced-Raman-Scattering (SERS) taken of two different individual, optically trapped *Bacillus stearothermophilus* (ATCC 7953) endospores.

Shown in FIG. 4B are SERS spectra representing two different *Bacillus stearothermophilus* (ATCC 7953) endospores. Only two spectra are shown for clarity. These spectra are constituted by pronounced bands at 585, 995, 1348 and 1668. Although, the plotted spectra are similar in shape over the measured spectral range (300 to 2200 cm$^{-1}$), large intensity variations are obvious between spectra A and B especially in the short-Stokes shifted (from 300 to about 1300 cm$^1$) spectral features. Additionally, a strong band at 1575 cm$^{-1}$ is present in spectrum A but absent in spectrum B. Further, a band in the "ring-breathing" region at 995 cm$^{-1}$ which is attributed to dipicolinic acid is blue shifted 10 cm$^{-1}$ from the spectra in FIG. 4A. This shift infers that dipicolinic acid occurs in a slightly different chemical environment in the two different *Bacillus stearothermophilus* strains (namely, ATCC 10149 and ATCC 7953) studied. Moreover, the pronounced band at 585 cm$^{-1}$ as well as the DPA band shift around 1000 cm$^{-1}$ implies that the composition of *Bacillus stearothermophilus* (ATCC 7953) is significantly different than that of *Bacillus stearothermophilus* (ATCC 10149).

EXAMPLE 8

Figure 5:
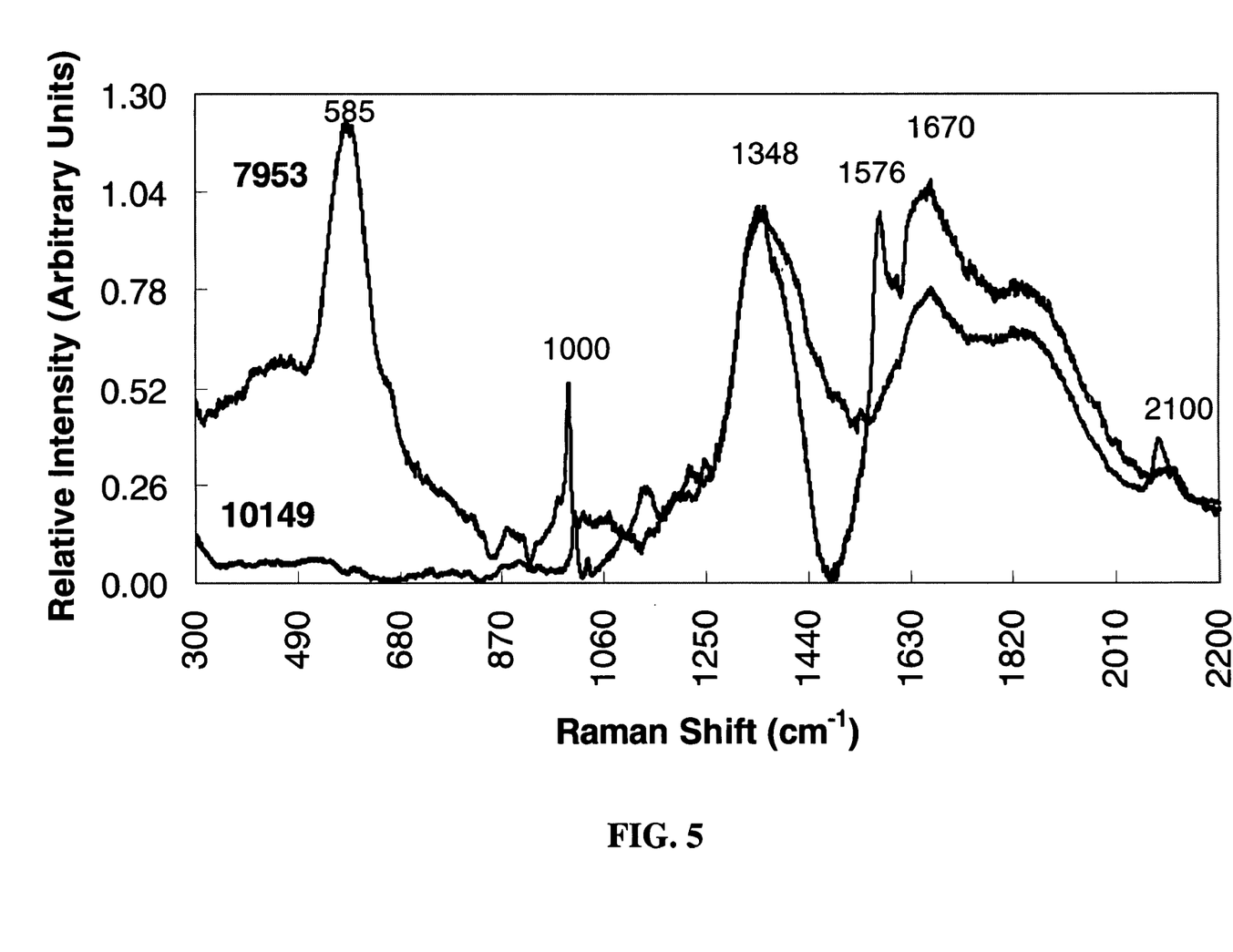
FIG. 5 is a graph of intensity normalized Surface-Enhanced-Raman-Scattering (SERS) spectra of an individual, optically trapped *Bacillus stearothermophilus* spore (ATCC 10149) and an individual, optically trapped *Bacillus stearothermophilus* spore (ATCC 7953).

The SERS spectral differences between the *Bacillus stearothermophilus* endospores studied are more apparent in FIG. 5, where averaged SERS spectra for *Bacillus stearothermophilus* (ATCC 7953) and *Bacillus stearothermophilus* (ATCC 10149) intensity normalized at 1348 cm$^{-1}$. As illustrated, these spectra have common features near 1348, 1670 and 1860 cm$^{-1}$. However, more importantly the ATCC 7953 spectrum is distinguishable from ATCC 10149 by pronounced bands at 585 and 1576 cm$^{-1}$. That is, these bands are present in the ATCC 7953 spectrum but absent in the ATCC 10149 spectrum. In addition, the ATCC 10149 spectrum shows a pronounced band near 2100 cm$^{-1}$ that is less obvious in the 7953 spectrum. Further, inspection of the "ring-breathing" region (near 1000 cm$^{-1}$) demonstrates a shift from 995 cm$^{-1}$ in the ATCC 7953 spectrum to 1005 cm$^{-1}$ in the ATCC 10149 spectrum. These data show the ability of the present invention to facilitate the strain-level discrimination of Bacillus stearothermophilus spores.

REFERENCES

1. A. Ashkin, *Physical Review Letters*, 24, 156, (1970).
2. A. Ashkin, J. M. Dziedzic, J. E. Bjorkholm, and S. Chu, *Optics Letters*, 11, 288, (1986).
3. A. Ashkin and J. M. Dziedzic, *Science*, 235, 1517, (1987).
4. A. Ashkin, J. M. Dziedzic, and T. Yamane, *Nature*, 320, 769, (1987).
5. A. Ashkin, K. Schutze, J. M. Dziedzic, U. Euteneuer and M. Schliwa, *Nature*, 348, 346, (1990).
6. W. H. Wright, G. J. Sonek, Y. Tadir, and M. W. Berns, 26, 2148, (1990).
7. M. Ericsson, D. Hanstorp, P. Hagberg, J. Enger, and T. Nystrom, 182, 5551, (2000).
8. C. Xie, M. A. Dinno, and Y. Li, *Optics Letters*, 27, 249, (2002).

9. J. Guck, R. Ananthakrishnan, H. Mahmood, T. J. Moon, C. C. Cunningham, and J. Kas, *Biophysical Journal,* 81, 767, (2001).
10. A. Resnick, *Review of Scientific Instruments,* 72, 4059, (2001).
11. M. Lankers, J. Popp, G. Rossling, and W. Kiefer, *Chemical Physics Letters,* 277, 331, (1997).
12. J. F. Lubben, C. Mund, B. Schrader, and R. Zellner, *Journal of Molecular Structure,* 480-481, 311, (1999).
13. V. E. Roman, J. Popp, E. Urlaub, S. Schlucker, M. Lankers, G. Robling, and W. Kiefer, *Journal of Molecular Structure,* 482-483, 497, (1999).
14. K. Ajito, M. Morita, and K. Torimitsu, *Analytical Chemistry,* 72, 4721, (2000).
15. K. Ajito and K. Torimitsu, *Applied Spectroscopy,* 56, 541, (2002).
16. M. P. Houlne, C. M. Sjorstrom, R. H. Uibel, J. A. Kleimeyer, and J. M. Harris, *Analytical Chemistry,* 74, 4311, (2002).
17. J. R. Ferraro and K. Nakamoto, *Introductory Raman Spectroscopy,* (Academic Press, San Diego and London, 1994), Chapter 3.
18. D. L. Gerrard J. G. Grasselli and B. J. Bulkin, *Organic and Petrochemical Applications of Raman Spectroscopy,* (John Wiley and Sons, Inc., New York, 1991), 301-304.
19. K. Grabar, R. G. Freeman, M. B. Hommer, and M. J. Natan, *Analytical Chemistry,* 67, 735, (1995).
20. W. H. Woodruff, T. G. Spiro and C. Gilvarg, *Biochemical and Biophysical Research Communications,* 58, 197, (1974).
21. H. Shibata, S. Yamashita, M. Ohe, and I. Tani, *Microbiology and Immunology,* 30, 307, (1986).
22. R. Manoharan, E. Ghiamati, R. Dalterio, K. A. Britton, W. H. Nelson and J. F. Sperry, *Journal of Microbiological Methods,* 11, 1, (1990).
23. E. Ghiamati, R. Manoharan, W. H. Nelson and J. F. Sperry, *Applied Spectroscopy,* 46, 357, (1992).
24. M. O. Scully, G. W. Kattawar, R. P. Lucht, T. Opatrny, H. Pilloff, A. Rebane, A. V. Sokolov and M. S. Zubairy, *Proceedings of the National Academy of Sciences of the United States of America,* 99, 10994, (2002).
25. A. E. Grow, L. L. Wood, J. L. Claycomb and P. A. Thompson, *Journal of Microbiological Methods,* 53, 221, (2003).
26. L. G. Olson, Y. S. Lo, T. P. Beebe, Jr and J. M. Harris, *Analytical Chemistry,* 73, 4268, (2001).
27. G. W. Gould and A. Hurst, *The Bacterial Endospores,* (Academic Press, London and New York, 1969), Chapter 7.
28. L. Dawei, W. Jian, X. Houwen, S. Xu and L. Fan-Chen, *Spectrochimica Acta,* 43A, 379, (1987).
29. X. Wang, H. Wen, T. He, J. Zuo, C. Xu and L. Fan-Chen, *Spectrochimica Acta,* 53A, 2495, (1997).
30. Sekulic, S.; Seashultz, M. B.; Wang, Z.; Kowalski, B. R.; Lee, S. E.; Holt, B. R. *Anal. Chem.* 1993, 65, 835A.
31. Lindberg, W.; Persson, J. A.; Wold, S. *Anal. Chem.* 1983, 55, 643.
32. Haaland, D. M.; Thomas, E. V. *Anal. Chem.* 1988, 60, 1193.
33. Haaland, D. M. *Anal. Chem.* 1988, 60, 1208.
34. Martens, H.; Naes, T. *Multivariate Calibration* John Wiley and Sons: New York, 1989.

Any patents or publications mentioned in this specification are indicative of the levels of those skilled in the art to which the invention pertains. These patents and publications are herein incorporated by reference to the same extent as if each individual publication was specifically and individually indicated to be incorporated by reference One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A method of particle detection comprising:
   optically trapping a single particle having an averaged linear dimension of between 0.10 microns and 50 microns in a focal region optical trap formed from a visible to near-infrared trap wavelength, said trap being proximal to a substrate having thereon a discontinuous metal coating that generates a plasmon electric field upon irradiation by an interrogation wavelength;
   exposing said single particle to the interrogation wavelength thereby producing a scattering spectrum relating to said particle and enhanced by said plasmon electric field; and
   collecting the scattering spectrum relating to said particle.

2. The method of claim 1, wherein said trap wavelength and said interrogation wavelength are the same wavelength.

3. The method of claim 2, wherein said trap wavelength and said interrogation wavelength are between 650 and 1100 nanometers.

4. The method of claim 1, wherein said trap wavelength and said interrogation wavelength are different.

5. The method of claim 4, wherein an intersection between said trap wavelength and said interrogation wavelength with said particle defines an angle of between 0 and 20 degrees inclusive.

6. The method of claim 1 further comprising, including within said trap an additive selected from the group consisting of: a second particle, a reactant towards said single particle, a metabolite of said single particle, and a toxin towards said single particle.

7. The method of claim 1 further comprising, moving said particle relative to said substrate and collecting a second scattering spectrum relating to said particle.

8. The method of claim 7 further comprising, relating said spectrum and said second spectrum to a dimensional structure of said particle.

9. The method of claim 1 further comprising, repeating the collecting step and varying the identity of said particle between repetitions to build a library of enhanced particle scattering spectra.

10. The method of claim 9 further comprising applying a chemometric analysis to a spectrum of an unknown particle relative to said library to identify relations to particle spectra.

11. The method of claim 1, wherein said particle is selected from the group consisting of: eukaryotic cells, bacteria, viruses, polymer strands, organelles, colloids, antibodies, ribosomes, nanocrystals, each alone or adhered as an aggregate particle.

12. The method of claim 1, wherein said trap is created within a microfluidic chamber in integrating said substrate and in fluid communication with a liquid sample containing at least one of said particle.

* * * * *